United States Patent [19]
Boyer et al.

[11] 3,975,408
[45] Aug. 17, 1976

[54] COLOR STABILIZATION OF REFINED DICARBOXYLIC ACID ANHYDRIDES

[75] Inventors: Ronald J. Boyer, Crystal City; Raymond E. Stenseth, St. Louis, both of Mo.; Richard J. Sheehan, Palos Hills, Ill.

[73] Assignee: Monsanto Company, St. Louis, Mo.

[22] Filed: Oct. 31, 1972

[21] Appl. No.: 302,624

Related U.S. Application Data

[63] Continuation-in-part of Ser. No. 41,116, May 27, 1970, abandoned.

[52] U.S. Cl. ............................................. 260/346.8 R
[51] Int. Cl.$^2$ ................................................ C07D 307/60
[58] Field of Search .................. 260/346.8 M, 346.8

[56] References Cited
UNITED STATES PATENTS

| | | | |
|---|---|---|---|
| 2,296,218 | 9/1942 | Middleton | 260/343 |
| 2,425,509 | 8/1947 | Clifford et al. | 260/346.8 |
| 2,432,470 | 12/1947 | Clifford | 260/346.8 |
| 3,564,022 | 2/1971 | Manoff et al. | 260/346.8 M |
| 3,586,703 | 6/1971 | Martinez et al. | 260/346.8 M |
| 3,775,436 | 11/1973 | Stenseth | 260/346.8 |

*Primary Examiner*—Harry I. Moatz
*Attorney, Agent, or Firm*—N. E. Willis; J. E. Maurer; F. D. Shearin

[57] ABSTRACT

Refined dicarboxylic acid anhydrides such as maleic anhydride are provided with improved color stability by a treating agent selected from the group consisting of chlorine and halides or elements in group IV*b* of the periodic table, the transition elements, vanadium, chromium, manganese, mercury, silicon, phosphorus, bismuth, antimony, lead, cerium and sulfur.

8 Claims, No Drawings

3,975,408

COLOR STABILIZATION OF REFINED DICARBOXYLIC ACID ANHYDRIDES

CROSS-REFERENCES TO RELATED APPLICATIONS

This application is a continuation-in-part of application Ser. No. 41,116, filed May 27, 1970 and now abandoned.

BACKGROUND OF THE INVENTION

This invention relates to the color stabilization of refined dicarboxylic acid anhydrides. More particularly, it relates to the color stabilization of refined maleic anhydride.

Anhydrides of certain dicarboxylic acids are available to the consumer in either solid or molten form. Although these anhydrides are classified as chemically stable compounds, some discoloration of the solid material may be detected after extended storage periods. This rate of discoloration is more pronounced when the solid anhydrides are maintained in their molten state for extended periods at elevated temperatures.

Maleic anhydride, for example, is often shipped in molten form in heated, insulated tank cars and is thus maintained in this state for long periods of time. Under such conditions, the molten maleic anhydride will frequently darken and become discolored.

Maleic anhydride can be prepared by the vapor-phase oxidation of organic compounds such as benzene, toluene, naphthalene, methyl naphthalene, phenol, cresol, benzophenone, furan, biphenyl, furfural, n-butane, 1-butene, 2-butene, butadiene, heptane, isooctane, crotonaldehyde and crotonic acid, employing a large excess of air. By-products of the above reaction include other organic acids, chromogenic bodies, carbon monoxide, carbon dioxide and water. Crude maleic anhydride is generally very dark in color, and although the crude maleic anhydride can be refined to a substantially color-free material, color reappears upon storage as hereinabove described. Color is an undesirable characteristic of maleic anhydride and, if present before or during processing, can cause deleterious effects in resulting products, such as plastics, where proper color is an important feature of the material.

The prior art discloses various methods for refining crude maleic anhydride to obtain a high grade product of low color. One such method is disclosed in U.S. Pat. No. 2,296,218 to Middleton, wherein crude maleic anhydride containing volatile color-imparting compounds produced as byproducts in the partial oxidation of organic compounds is treated in the liquid state with a modification agent selected from the group consisting of the oxides and hydroxides of sodium, potassium, lithium, calcium, zinc and magnesium, and the halides of zinc, iron and aluminum and reaction products thereof. Thereafter, the treated maleic anhydride is subjected to distillation, leaving the darkening impurities in the distillation residue.

Another method for improving color stability is disclosed in U.S. Pat. No. 3,115,503 wherein color stabilizing amounts of ethylenediaminetetraacetic acid are added to a molten cyclic anhydride during the preparation process or thereafter. Alternatively, the acid is added to the finely divided solid cyclic anhydride prior to compressing into tablets or briquets.

Another method is taught in U.S. Pat. No. 3,596,703 wherein small amounts of a stabilizer are incorporated into maleic anhydride. The stabilizers used included hydrochloric acid, hydrobromic acid, silver chloride, barium nitrate, alkali or alkali metal sulfates, chlorides or bromides. Similar compounds were found to have no usefulness as stabilizers.

SUMMARY OF THE INVENTION

Despite the known prior art efforts toward improving the color stability of dicarboxylic acid anhydrides, there remains a need for further improvement. It is an object of the present invention, therefore, to provide color-stabilized dicarboxylic acid anhydrides. Another object of the present invention is to provide a color-stabilized composition comprising a dicarboxylic acid anhydride and a color-stabilizing amount of a treating agent. Still another object of the present invention is to significantly retard discoloration of solid and molten dicarboxylic acid anhydrides during storage. Yet another object of the present invention is to provide a process for color stabilization of refined dicarboxylic acid anhydrides, such as maleic anhydride, by the introduction of novel treating agents.

These and other objects are achieved by introducing into refined maleic anhydride a color-stabilizing amount of a treating agent to form a composition comprising a major amount of refined maleic anhydride and a color-stabilizing amount of a treating agent selected from at least one of the group consisting of chlorine and halides of elements in group IVb of the periodic table, the transition elements, vanadium, chromium, manganese, mercury, silicon, phosphorus, bismuth, antimony, lead, cerium and sulfur.

For the purposes of this invention, the term "transition elements" is defined as those elements in group VIII of the periodic table which are grouped together in trios, viz: iron, cobalt, nickel; ruthenium, rhodium, palladium; and osmium, iridium, platinum. The phrase "ionic halogen" is defined herein as a halogen capable of existing in the form of an ion. The term "group IV*b* elements" refers to those elements in group IV*b* of the periodic table, viz: titanium, zirconium and hafnium. The term "refined maleic anhydride" refers to that maleic anhydride having very little or no color that is suitable for use in commerce without further purification steps.

Color stabilized compositions obtained through use of the treating agents of this invention exhibit superior color properties as will be demonstrated by test results hereinafter presented.

In addition to chlorine as a treating agent, it has been discovered that selected inorganic compounds containing an ionic halogen are superior treating agents for color stabilization of refined dicarboxylic acid anhydrides. Although not to be construed in a limiting sense, the following halogen-containing inorganic compounds have exhibited color stabilizing effects when employed as treating agents for refined maleic anhydride: ammonium chloride, chromic chloride, manganese chloride, ferric chloride, ferric bromide, cobalt chloride, cobalt bromide, cadmium chloride, aluminum chloride, thorium tetrachloride, mercuric chloride, mercurous chloride, lead chloride, silicon tetrachloride, phosphorus trichloride, bismuth chloride, antimony chloride, strontium chloride, titanium tetrachloride, auric chloride, zirconium tetrachloride, sulfurous oxychloride, silver tetrafluoroborate, potassium chloroplatinate, rhodium chloride, nickel chloride, cupric chloride, zinc chloride and phosphorus oxychloride.

The halogen-containing treating agents of the present invention are employed with dicarboxylic acid anhydrides in the refined state such as commercially pure maleic anhydride. This simplifies the method of introducing the treating agent in contrast to many prior art methods wherein the color stabilizer must be added to the crude anhydride during processing. The prior art methods of introducing a color stabilizer during processing generally result in the polymerization or carbonization of impurities, thus making them separable by distillation. The present invention is distinguished therefrom in that no distillation after treatment is necessary in the method described herein.

It has been found that dicarboxylic acid anhydrides can be color stabilized by treatment with the treating agents of the present invention according to numerous procedures. Successful results have been achieved by treating molten refined maleic anhydride in the pipeline at the manufacturing site using a filter bed technique. According to this technique, a filter assembly is installed in the pipeline and is adapted for introduction of the treating agent on the upstream side of the filter. The flowing maleic anhydride is thus contacted with the treating agent, and the filter removes the excess treating agent from the maleic anhydride as the latter flows downstream in the pipeline. When a filter system is thus provided in the treating step, an excess of treating agent can advantageously be employed without danger of undissolved particles remaining in the treated product. The presence of excess treating agent achieves the desired results with lower residence times in contacting the flowing maleic anhydride. However, successful results have also been achieved by treating batches of molten, refined maleic anhydride with an excess of treating agent and thereafter filtering out the non-solubilized treating agent.

It is sometimes desirable to treat refined molten maleic anhydride in the melting kettle or in a heated tank car. If the treated product is not filtered thereafter, an excess of treating agent should be avoided during the treating step.

It is to be recognized that there is some variation in properties among different lots and sources of maleic anhydride. Furthermore, it has been found that some lots of maleic anhydride are more difficult to treat than others. Accordingly, there will be some variation in the optimum amount of treating agent solubilized in the treated product depending upon the product and the treating agent selected. Thus, the concentration of the treating agent within the treated product may vary from a trace amount as for example 0.01 parts per million by weight, to 1,000 parts per million by weight or greater. Generally, from 0.01 to 100 parts per million by weight is sufficient. In order to maintain clarity in the treated maleic anhydride compoisiton, it is important that substantially all of the treating agent therewithin be in solution, an excess being avoided so that haze and precipitates will not be formed.

DESCRIPTION OF THE PREFERRED EMBODIMENTS

The following examples illustrate the advantageous and unexpected results that are achieved through use of the treating agents of this invention. These examples are intended to be illustrative only and are not to be construed in a limiting sense.

EXAMPLES 1 THROUGH 31

Examples 1 through 31 demonstrate the effectiveness of chlorine and a variety of halogen-containing treating agents in improving the heat stability of refined maleic anhydride.

Untreated samples from a given lot of commercially pure maleic anhydride were melted in a 25 mm. by 200 mm. test tube and the initial or "melt" colors were determined at sample temperatures from about 55° to about 70°C. by comparison with the APHA color standards. The standard used to indicate the quantity or intensity of color of products in solution form is known as the APHA standard color test. This test is one developed by the American Public Health Association and is known as the Hazen Platinum Cobalt Scale, a description of which is found in volume 2, part 13, page 2425 of the 6th edition of STANDARD METHODS OF CHEMICAL ANALYSIS by F. J. Welcher, editor.

Temperatures of the untreated samples were then raised to 140°C. and color values were determined after 2 hours, 4 hours, 6 hours and 24 hours of heating. The color values for the untreated maleic anhydride samples from a number of tests were averaged and are presented in Table I below where the treating agent is indicated as "None". After 4 hours at 140°C., the average APHA color of all untreated samples was 500. The average initial or "melt" color was 15.

Likewise, additional samples of the aforementioned maleic anhydride were melted and treated with chlorine or various halogen-containing treating agents within the scope of the present invention. APHA color determinations for each of the 31 treated samples were made in the manner described above. These APHA color determinations are presented in Table I below. Except as noted, the halogen-containing treating agent was added to the molten maleic anhydride at a concentration of 50 parts per million. Where the phrase "parts per million" is used herein, the "parts" are parts by weight based upon the weight of the maleic anhydride.

TABLE I

| Example No. | Treating Agent | APHA Melt Color | APHA COLOR AT 140°C | | | |
|---|---|---|---|---|---|---|
| | | | 2 Hrs. | 4 Hrs. | 6 Hrs. | 22-24 Hrs. |
| | None | 15 | 300 | 500 | — | — |
| 1 | Chlorine[a] | 20 | 60 | 65 | 85 | 150 |
| 2 | Aluminum chloride | 30 | 125 | — | — | 500 |
| 3 | Ammonium chloride | 15 | 50 | 125 | 300 | 500 |
| 4 | Antimony chloride | 15 | 25 | 30 | 35 | 70 |
| 5 | Auric chloride[b,c] | 35 | 100 | 125 | 150 | 275 |
| 6 | Bismuth chloride[c,d] | 15 | 25 | 35 | 40 | 60 |
| 7 | Cadmium chloride | 10 | 100 | 125 | 140 | 500 |
| 8 | Cerous chloride | 15 | 40 | 50 | 70 | 150 |
| 9 | Chlorosulfonic acid[d] | 15 | 30 | 150 | 250 | 500+ |
| 10 | Chromic chloride[c] | 10 | 25 | 30 | 50 | 125 |
| 11 | Cobalt bromide | 20 | 30 | 40 | 45 | 90 |

TABLE I-continued

| Example No. | Treating Agent | APHA Melt Color | APHA COLOR AT 140°C | | | |
|---|---|---|---|---|---|---|
| | | | 2 Hrs. | 4 Hrs. | 6 Hrs. | 22-24 Hrs. |
| 12 | Cobalt chloride | 10 | 15 | 30 | 35 | 110 |
| 13 | Cupric chloride | 10 | 100 | 135 | 150 | 300 |
| 14 | Ferric bromide[e] | 30 | 30 | 35 | 40 | 90 |
| 15 | Ferric chloride[e] | 40 | 85 | 90 | 95 | 175 |
| 16 | Hexaminocobaltic chloride | 20 | 50 | 70 | 90 | 200 |
| 17 | Lead chloride | 15 | 30 | 50 | 70 | 150 |
| 18 | Manganese chloride | 15 | 25 | 30 | 30 | 60 |
| 19 | Mercuric chloride | 15 | 25 | 30 | 40 | 80 |
| 20 | Mercurous chloride | 15 | 40 | 60 | 70 | 125 |
| 21 | Nickel chloride | 10 | 25 | 40 | 60 | 100 |
| 22 | Phosphorus oxychloride | 15 | 25 | 30 | 35 | 60 |
| 23 | Phosphorus trichloride[e] | 15 | 25 | 35 | 40 | 80 |
| 24 | Rhodium chloride | 15 | 30 | 40 | 45 | 90 |
| 25 | Silicon tetrachloride[e] | 15 | 25 | 30 | 35 | 80 |
| 26 | Silver tetrafluoroborate | 15 | 100 | 150 | 500+ | — |
| 27 | Sulfurous oxychloride | 15 | 45 | 70 | 70 | 130 |
| 28 | Thorium tetrachloride | 15 | 60 | 80 | 90 | 125 |
| 29 | Zinc chloride | 20 | 35 | 40 | 60 | 350 |
| 30 | Titanium tetrachloride[e] | 10 | 20 | — | — | 60 |
| 31 | Zirconium tetrachloride | 15 | 25 | 30 | 40 | 90 |

[a] 50 ppm bubbled through sample
[b] 10 ppm added
[c] Saturated aqueous solution
[d] One crystal or drop added
[e] Several crystals added Thus, it can be seen that some inorganic halides, such as aluminum chloride and ammonium chloride, are marginally effective whereas other halogen-containing inorganic compounds impart outstanding color stabilization to refined maleic anhydride. The halides of titanium, chromium, manganese, iron, cobalt, nickel, zirconium, rhodium, mercury, silicon, phosphorus, bismuth and antimony have demonstrated superior results as color stabilizing treating agents for refined maleic anhydride.

Although the invention has been described in terms of specified embodiments which are set forth in considerable detail, it should be understood that this is by way of illustration only, and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed is:

1. A composition comprising a major amount of refined maleic anhydride and from about 0.01 to about 1,000 parts per million by weight, based on the weight of the maleic anhydride, of a treating agent selected from at least one of the group consisting of halides of titanium, zirconium, hafnium, cobalt, nickel, ruthenium, rhodium, palladium, osmium, iridium, platinum, vanadium, chromium, manganese, mercury, silicon, phosphorus, bismuth, antimony, lead, cerium, and sulfur.

2. A composition of claim 1 wherein the treating agent comprises from about 0.01 to about 100 parts per million by weight of the maleic anhydride.

3. A composition of claim 1 wherein the halides are chlorides.

4. A composition of claim 1 wherein the treating agent is cobalt chloride.

5. A composition of claim 1 wherein the treating agent is manganese chloride.

6. A composition of claim 1 wherein the treating agent is antimony chloride.

7. A composition of claim 1 wherein the treating agent is titanium tetrachloride.

8. A composition of claim 1 wherein the treating agent is silicon tetrachloride.

* * * * *